(12) United States Patent
Huang et al.

(10) Patent No.: US 8,515,002 B2
(45) Date of Patent: Aug. 20, 2013

(54) X-RAY DARK-FIELD IMAGING SYSTEM AND METHOD

(75) Inventors: Zhifeng Huang, Beijing (CN); Zhiqiang Chen, Beijing (CN); Li Zhang, Beijing (CN); Zhentian Wang, Beijing (CN); Yuxiang Xing, Beijing (CN); Ziran Zhao, Beijing (CN); Yongshun Xiao, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 99 days.

(21) Appl. No.: 13/147,952

(22) PCT Filed: Jul. 6, 2010

(86) PCT No.: PCT/CN2010/001010
§ 371 (c)(1),
(2), (4) Date: Aug. 4, 2011

(87) PCT Pub. No.: WO2011/003278
PCT Pub. Date: Jan. 13, 2011

(65) Prior Publication Data
US 2011/0293064 A1 Dec. 1, 2011

(30) Foreign Application Priority Data
Jul. 7, 2009 (CN) .......................... 2009 1 0088662

(51) Int. Cl.
*A61B 6/00* (2006.01)
(52) U.S. Cl.
USPC ..................................... 378/6; 378/7; 378/62
(58) Field of Classification Search
USPC .......................................... 378/7, 62
See application file for complete search history.

(56) References Cited

U.S. PATENT DOCUMENTS

| 7,046,757 B1* | 5/2006 | Bani-Hashemi et al. ......... 378/7 |
| 2010/0074395 A1* | 3/2010 | Popescu .......................... 378/16 |

(Continued)

FOREIGN PATENT DOCUMENTS

| CN | 201191275 Y | 2/2009 |
| CN | 200810166472.9 | 9/2009 |
| WO | WO2009076700 A1 | 6/2009 |

OTHER PUBLICATIONS

ZF Huang et al., National Radiation Digital Imaging and CT Newtechnology, Jun. 2009, Study for Hard-X-Ray Grating Dark-Field Imaging Technique Based on General X-Ray Machine Source.

(Continued)

*Primary Examiner* — Alexander H Taningco
(74) *Attorney, Agent, or Firm* — Brinks Hofer Gilson & Lione

(57) ABSTRACT

An x-ray imaging technology, performing an x-ray dark-field CT imaging of an examined object using an imaging system which comprises an x-ray source, two absorbing gratings G1 and G2, an x-ray detector, a controller and a data processing unit, comprising the steps of: emitting x-rays to the examined object; enabling one of the two absorbing gratings G1 and G2 to perform phase stepping motion within at least one period range thereof; where in each phase stepping step, the detector receives the x-ray and converts it into an electric signal; wherein through the phase stepping of at least one period, the x-ray intensity at each pixel point on the detector is represented as an intensity curve; calculating a second moment of scattering angle distribution for each pixel, based on a contrast of the intensity curve at each pixel point on the detector and an intensity curve without presence of the examined object; taking images of the object at various angles, then obtaining an image with scattering information of the object in accordance with a CT reconstruction algorithm.

16 Claims, 3 Drawing Sheets

(56) References Cited

U.S. PATENT DOCUMENTS

| | | | |
|---|---|---|---|
| 2010/0220832 A1* | 9/2010 | Ning et al. | 378/4 |
| 2010/0246765 A1* | 9/2010 | Murakoshi et al. | 378/62 |
| 2010/0272235 A1* | 10/2010 | Takahashi | 378/62 |
| 2010/0290590 A1* | 11/2010 | Ouchi et al. | 378/62 |

OTHER PUBLICATIONS

F. Pfeiffer et al., Nature Materials, vol. 7, Feb. 2008, Hard-X-Ray Dark-Field Imaging Using a Grating Interferometer.

* cited by examiner

X-RAY DARK-FIELD IMAGING SYSTEM AND METHOD

The present application is the national phase application of PCT Application No. PCT/CN2010/001010, filed Jul. 6, 2010, which claims priority to Chinese Patent Application No. 200910088662.8, filed Jul. 7, 2009, the entireties of both of which are hereby incorporated by references.

TECHNICAL FIELD

The present invention relates to x-ray imaging field, and specifically to a technology of performing dark-field imaging of an object using x-rays.

BACKGROUND

In prior art devices such as CT, scanning imaging of an object using x-rays has been widely used. However, the traditional x-ray imaging examines the internal structure of an object without destruction by using attenuation property of a material for x-rays, and this belongs to x-ray bright-field imaging technology.

In optical imaging field, dark-field imaging is remarkably different from bright-filed imaging. Dark-field imaging is a technology of imaging a substance using non-direct light (e.g. scattered light, diffracted light, refracted light, fluorescent light, etc.). Therein, the study of visible light and electron dark-field imaging technology started relatively early, which has been widely used in scientific research, industrial field, medical field, biological field and so on. In hard x-ray imaging field, traditional hard x-ray imaging technology performs the imaging of an object using direct x-rays, i.e. using the bright-field imaging technology. As for dark-field imaging, due to the particular optical properties of hard x-rays, the manufacture of required optical elements is very difficult, and accordingly, the hard x-rays dark-field imaging can hardly be better fulfilled all along. In the 90s of the twentieth century, as the third-generation synchronous radiation source develops and the manufacturing level of delicate hard x-ray optical elements rises, the study of hard x-ray dark-field imaging technology gains certain growth, but as compared with the hard x-ray phase contrast imaging technology rising simultaneously, the hard x-ray dark-field imaging technology has always been insufficiently noticed due to low semaphore, comparatively difficult detection, long time of imaging, etc.

However, the hard x-ray dark-field imaging technology is originally advantageous over the bright-field imaging and the phase contrast imaging in terms of capabilities for distinguishing and detecting an internal fine structure of a substance. The hard x-ray dark-field imaging technology performs the imaging of the internal structure of the substance based on a difference in scattering capability of the substance for x-rays. Since the scattering of hard x-rays is at a scale of micrometer magnitude or even nanometer magnitude, the hard x-ray dark-field imaging technology can enable viewing of an internal ultrafine structure of the substance, which is undistinguishable for hard x-ray bright-field imaging and phase contrast imaging.

In recent years, researchers propose applying the hard x-ray dark-field imaging technology based on crystal used for synchronous radiation sources to cartilage tissue diagnosis and early breast cancer diagnostic imaging, and this achieves an image effect superior to the hard x-ray bright-field imaging. However, since the synchronous radiation device has a large volume, costs much and enables a small field of view, it confines the hard x-ray dark-field imaging technology to great extent in terms of applications in medical clinics and industrial detection.

Grating imaging technology was born in 2006, releasing the hard x-ray dark-field imaging from restraint by and dependence on the synchronous radiation source. With an all-purpose x-ray apparatus, it enables a hard x-ray dark-field imaging with a large field of view, and this largely reduces the difficulty facing the application of the hard x-ray dark-field imaging technology. At the beginning of 2008, Pfeiffer, et al. from Switzerland realized a hard x-ray dark-field imaging with a large field of view (e.g. 64 mm×64 mm) by use of gratings based on a Talbot-Lau interferometry method on an all-purpose x-ray apparatus. Such a grating-type hard x-ray dark-field imaging technology is capable of well distinguishing between plastic and rubber materials and of enabling view of bones in chicken wings and ultrafine structures in muscle tissues. Starting from 2006, Huang Zhifeng, et al. from Tsinghua University have conducted related studies on grating-type hard x-ray phase contrast imaging technology based on an all-purpose x-ray apparatus, and proposed a grating phase contrast imaging method based on projection in incoherent condition in the Chinese patent application No. 200810166472.9, filed in 2008 and titled "X-ray Grating Phase Contrast Imaging System and Method", establishing an experimental platform for grating phase contrast imaging based on an all-purpose x-ray apparatus. All contents of the patent application are introduced into the present application by reference.

SUMMARY OF THE INVENTION

On the basis of the classic-optics-based x-ray grating phase contrast imaging method that has been proposed, the present invention sets forth a classic-optics-based x-ray dark-field imaging system and method based on the classic-optics-based x-ray grating imaging technology.

According to the present invention, scattering information of an object is reflected by a decrease in the contrast ratio of displacement curves in a grating-based system, and the present invention derives a quantitative relationship between a second moment of distribution of the scattered radiations after passing through the substance and the contrast ratio decrease of the displacement curves in the grating imaging system, and may quantitatively reconstruct the scattering information of the object based on a traditional linear CT reconstruction algorithm.

According to one aspect of the present invention, an x-ray imaging system is provided for performing an x-ray scattering imaging of an object, comprising: an x-ray source, a first and a second absorbing gratings G1 and G2, and an x-ray detector, which are orderly located in a propagation direction of the x-rays;

wherein, the system further comprises:

a data processor unit for processing data information; and a controller for controlling operations of said x-ray source, first and second absorbing gratings G1 and G2, x-ray detector and processor unit, to carry out the following process:

the x-ray source emits x-rays to an examined object; one of the two absorbing gratings G1 and G2 performs phase stepping motion within at least one period range thereof; in each phase stepping step, said detector receives the x-ray and converts it into an electric signal; wherein through the phase stepping of at least one period, the x-ray intensity at each pixel point on the detector is represented as an intensity curve; the intensity curve at each pixel point on the detector is compared to an intensity curve without the presence of the examined object to acquire a variation in the contrast ratio of the intensity curves; a second moment of scattering angle distribution for each pixel on the detector is calculated from the intensity curve variation; and pixel values of an image of the examined object are obtained from the second moment of scattering angle distribution, whereby the image of the examined object is reconstructed.

In addition, it is preferable that said system further comprises a rotation device for enabling the examined object to rotate an angle relatively under the control of said controller. Therein, at each rotated angle, the respective steps described above are repeated such that x-ray scattered images at multiple angles are obtained. In accordance with the traditional linear CT image reconstruction algorithm, such as filtered back projection algorithm, the image of the examined object can be reconstructed then.

Specifically, a contrast ratio of said intensity curve is represented as:

$$V = \frac{I_{max} - I_{min}}{I_{max} + I_{min}}$$

Therein, $I_{max}$ and $I_{min}$ represent respectively the maximum and the minimum values of the intensity curve.

And, the quantitative relationship between the second moment $\sigma^2$ of scattering distribution and the contrast ratio of said intensity curve is:

$$\sigma^2 = -\frac{1}{2\pi^2}\left(\frac{p_2}{D}\right)^2 \ln\left(\frac{V_s}{V_r}\right)$$

Therein, $V_s$ and $V_r$ represent respectively contrast ratios of the intensity curves at a certain point on the detector with and without the presence of the examined object, $p_2$ is the period of the second absorbing grating G2, and D is a distance between said first and second absorbing gratings.

Further, the CT image reconstruction algorithm uses the following formula:

$$\sigma^2 = \int_L f_s(l)\,dl = \int_L \frac{\rho_n(l)\sigma_s(l)}{2\alpha_p}\,dl$$

Wherein $\rho_n$ is a substance density, $\sigma_s$ is a scattering cross section, and $\alpha_p$ is a broadening width of a single spherical scattering body for radiation. It can be seen that a generalized scattering parameter is associated with such physical quantities as substance density $\rho_n$, scattering cross section $\sigma_s$, broadening width $\alpha_p$ of a single spherical scattering body for radiation, etc..

According to another aspect of the present invention, an x-ray imaging method is provided for imaging an object using an x-ray grating imaging system, wherein the x-ray grating imaging system comprises: an x-ray source, a first and a second absorbing gratings G1 and G2, an x-ray detector, a controller and a data processing unit; wherein, the method includes the steps of: emitting x-rays to an examined object; enabling one of the two absorbing gratings G1 and G2 to perform phase stepping motion within at least one period range thereof; where in each phase stepping step, the detector receives the x-ray and converts it into an electric signal; wherein through the phase stepping of at least one period, the x-ray intensity at each pixel point on the detector is represented as an intensity curve; comparing the intensity curve at each pixel point on the detector to an intensity curve without the presence of the examined object to acquire a variation in the contrast ratio of the intensity curves; calculating a second moment of scattering angle distribution for each pixel on the detector from the intensity curve variation; and obtaining pixel values of an image of the examined object from the second moments of scattering angle distribution, whereby the image of the examined object is reconstructed.

A classic-optics-based grating dark-field imaging system may be applied to material science, medical imaging of tissues (e.g. breast) and other fields alike. Moreover, the principle revealed by the present invention is equally applicable to the reconstruction in an interference grating dark-field imaging method.

DESCRIPTION OF THE DRAWINGS

FIG. 3 shows multi-information images extracted by the classic-optics-based x-ray grating imaging system, wherein FIG. 3a is an image of absorption, FIG. 3b is an image of differential phase information, and FIG. 3c is an image of dark-field information.

FIG. 4 shows CT reconstructed images from the classic-optics-based x-ray grating imaging system, wherein FIG. 4a is an image of absorption, FIG. 4b is an image of differential phase information, and FIG. 4c is an image of dark-field information; wherein the reconstructed fault planes are respectively identified with white lines in FIG. 3.

EMBODIMENTS

Figure 1:
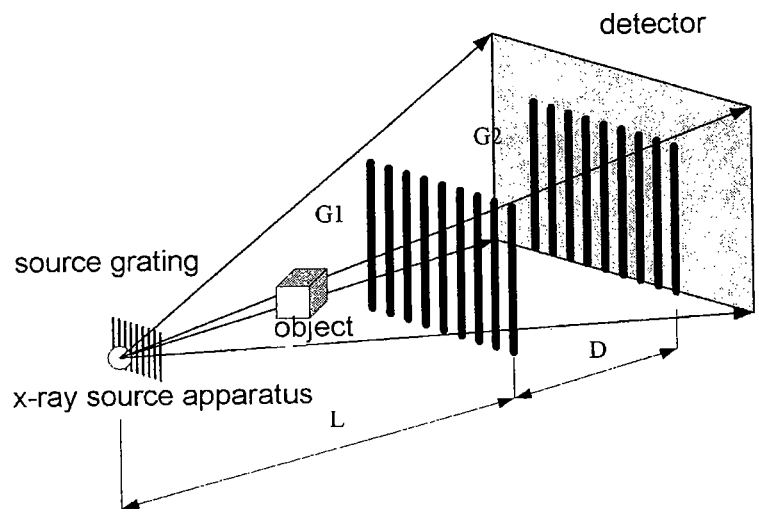
FIG. 1 is a schematic diagram of a classic-optics-based x-ray grating imaging system.

By reference to FIG. 1, according to the principle of the present invention, an x-ray grating dark-field imaging system comprises: an x-ray apparatus S, an optional source grating G0, two absorbing gratings (i.e. first and second absorbing gratings G1 and G2), and a detector, which are orderly positioned in a propagation direction of the x-rays. The x-ray apparatus may be an all-purpose x-ray generator.

Preferably, the cycle of the two absorbing gratings is between 0.1 and 30 μm. The gratings use heavy metal as the absorbing material, and to take gold (Au) for example, the height of the gold is determined by the x-ray energy applied, which is between 10 and 100 μm. For example, for x-rays of 20 keV, gold with a height of more than 16 μm can block 90% of the x-rays.

Preferably, the detector can be a matrix detector, wherein each detection unit (pixel) can detect the intensity variation of the incident x-rays.

Specifically, the x-ray apparatus is used for emitting x-ray beams to an examined object. In the case of an x-ray source with large focal spot, an additional source grating (e.g. a multi-slit collimator) may be added in front of the x-ray apparatus to produce a group of linear x-ray sources with small focal spot. The two absorbing gratings G1 and G2 have their cycles respectively set as $p_1$ and $p_2$, which are orderly positioned in parallel in the propagation direction of the x-ray beams. The detector is used for receiving x-rays and converting x-ray signals into digitally processable electric signals via a photoelectric signal conversion technology (e.g. digitalized photographing technology).

In addition, the x-ray grating dark-field imaging system should further comprise a data processing unit for calculating the intensity variation after the x-rays pass through the examined object from said electric signals, calculating the intensity contrast ratio decrease at each pixel on the detector based on said intensity variation information, thereby acquiring scattering information of the x-rays by the examined object, and calculating pixel information of the examined object based on the scattering information.

Further, the system comprises a controller (not shown) for controlling operations of said x-ray apparatus, absorbing gratings and processor unit. Preferably, said controller and said data processing unit may be integrated as a whole and implemented by an all-purpose or dedicated processor.

Furthermore, the system comprises an imaging unit (not shown) for reconstructing and displaying an image of the object based on said scattering information (scattering parameter(s) that may be embodied as pixel information of the examined object).

The x-ray beams emitted by the all-purpose x-ray apparatus may be fan beams, cone beams or parallel beams. Cone beams are preferred in the present invention. Thus, the imaging system in the present invention adopts two absorbing gratings whose cycles are preferably in a geometrical relationship, namely:

$$\frac{p_1}{p_2} = \frac{L}{L+D}$$

Therein, L is a distance from the radiation source (the source grating if it is present) to the first grating G1, and D is a distance between the two absorbing gratings G1 and G2.

Figure 5:
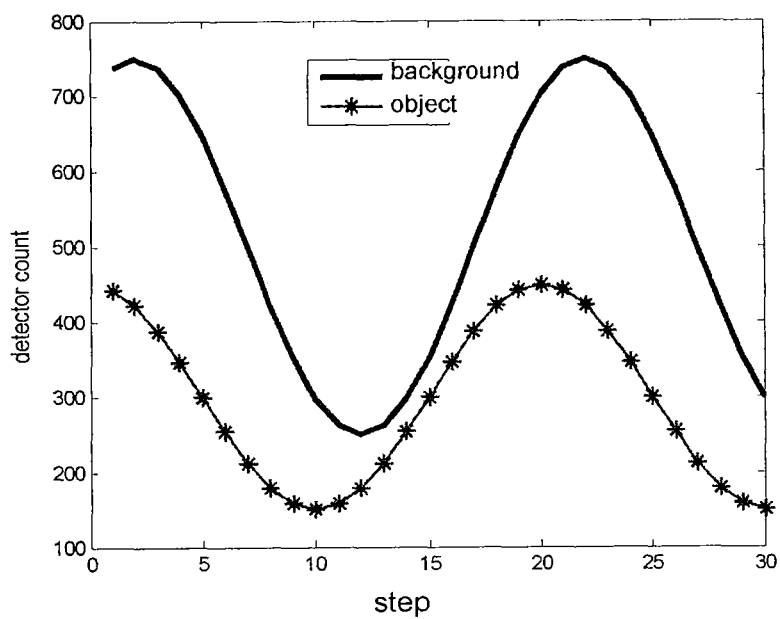
FIG. 5 is a schematic diagram showing x-ray intensity and contrast ratio variation after the x-rays pass through an examined object and are scattered thereby, the data in this figure is simulated data.

Based on the relative phase stepping motion of the two absorbing gratings, an intensity variation curve of x-rays received at a certain point on the detector can be obtained. As for the system shown in the figure, the two absorbing gratings (G1, G2) perform relative stepping motion: for example, grating G1 is fixed, while grating G2 moves N steps (N>1) translationally (sp) within a distance of the grating cycle $p_2$ along an X direction (which is orthogonal to the propagation direction of the x-rays) (or alternatively, grating G2 is fixed, while G1 steps along the X direction). Said detector collects image information each step the grating G2 moves in translation; after N images are collected within the translation distance, a distribution status of an intensity variation curve within one grating cycle for each pixel (each point on a detecting plane of the detector) on the detector can be obtained. As shown in FIG. 5, a shape of the intensity variation function resembles a sine or cosine function.

Figure 2:
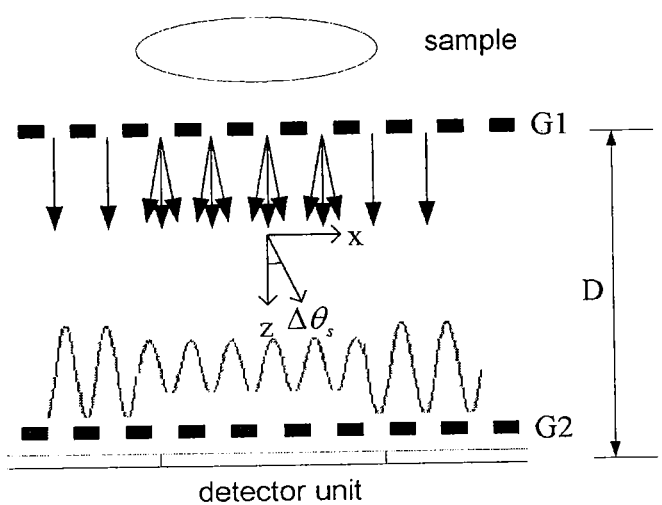
FIG. 2 is a schematic diagram of the principle of grating-based dark-field imaging.

By reference to FIG. 2, according to the grating-based dark-field imaging method of the present invention, when an x-ray beam passes through the object, it is broadened due to scattering by the object. An angular distribution function may be used to describe the x-ray scattered beams. As compared to the case without an examined object, namely a sample, the scattering causes a decrease in the contrast ratio of the projected grating stripes, which may be used to measure a scattering capability of the examined object for x-rays, namely the dark-field information.

Based on the relative phase stepping motion of the first or the second absorbing grating G1, G2, an x-ray intensity curve at a certain point on the detector with or without the presence of an examined object can be obtained, as shown in the figure. Therein, when there is no examined sample, an intensity curve at each point may be pre-known as background information, which information may be pre-stored in memory of the system or may temporarily be automatically acquired upon startup of the device. It can be seen that after x-rays are scattered by an examined object, the contrast ratio of the intensity curve at a point on the detector decreases by certain extent. Accordingly, scattering information of the examined object can be indirectly measured by measuring the decrease in the contrast ratio of the x-ray intensity curve.

Further, based on the phase stepping method, the measured sample intensity curve and the background intensity curve for a certain pixel on the detector may be approximately represented by cosinusoidal functions, i.e.:

$$I_s(k) \approx a_s + b_s \cos(k\Delta x + \phi_s) \quad (1)$$

$$I_b(k) \approx a_b + b_b \cos(k\Delta x + \phi_b) \quad (2)$$

Therein, $I_s(k)$ and $I_b(k)$ represent respectively the intensity values corresponding to a certain pixel point at the $k^{th}$ step in the phase stepping method with and without the examined sample, $\Delta x$ is a stepping length, and a phase difference between the displacement curves is $\Delta \phi = (\phi_s - \phi_b)$. $I_s$ is the intensity curve for a certain pixel point on the detector with the presence of the examined object, $I_b$ is the intensity curve for a certain pixel point on the detector without the presence of the examined object, $a_s$ is an average value of the intensity curve with the presence of the examined object, $b_s$ is the magnitude of the intensity curve with the presence of the examined object, $a_b$ is an average value of the intensity curve without the presence of the examined object, $b_b$ is the magnitude of the intensity curve without the presence of the examined object, $\phi_s$ is the phase of the intensity curve with the presence of the examined object, $\phi_b$ is the phase of the intensity curve without the presence of the examined object, and k represents the $k^{th}$ step.

Thus, the contrast ratio of the x-ray intensity curve at a certain pixel point on the detector may be represented as:

$$V = \frac{I_{max} - I_{min}}{I_{max} + I_{min}} \quad (3)$$

Therein, $I_{max}$ and $I_{min}$ represent respectively the maximum and the minimum values of the intensity curve.

In existing imaging systems, the size of a detector pixel is far larger than a cycle of a grating stripe, and a plurality of stripe cycles are contained in a detector pixel. Since a scattering angle distribution smaller than the size of the detector pixel is undistinguishable, we assume that the x-ray scattering angle distribution in each detector pixel is identical, and each may be represented by a Gaussian function, and a second moment of the Gaussian function reflects an intensity of broadening of the x-rays.

The inventor of the present application derives, under projection-based grating dark-field imaging technology, a quantitative relationship between the second moment $\sigma^2$ of the scattering angle distribution and the contrast ratio of two intensity curves as follows:

$$\sigma^2 = -\frac{1}{2\pi^2}\left(\frac{p_2}{D}\right)^2 \ln\left(\frac{V_s}{V_r}\right) \quad (4)$$

Therein, $V_s$ and $V_r$ represent respectively contrast ratios of the intensity curves at a certain pixel point on the detector with and without the presence of the examined object, $p_2$ is a cycle of G2, and D is a distance between the two absorbing gratings.

In the present invention, the second moment $\sigma^2$ of the scattering angle distribution obtained from formula (4) may be used for reconstructing an image of the object. Specifically, an x-ray scattered CT imaging of the examined object includes:

An examined subject, e.g. a human body, may rotate, for example, 360 degrees relative to the imaging system. Thus, it is necessary to provide a means for enabling the examined object to rotate relative to the entire system, which means is usually an electromechanical rotating structure and is controlled by a controller. The x-ray source emits x-rays to the object at each angle. Meanwhile, the two absorbing gratings of the system accomplish one stepping motion of at least one cycle. During this process, a second moment $\sigma^2$ of scattering angle distribution at each pixel on the detector is obtained by comparing variations in the contrast ratio of the intensity curve at each pixel point on the detector. Then, the object rotates an angle relatively, and the grating stepping motion described above is repeated to obtain a second moment $\sigma^2$ of scattering angle distribution at each pixel point at this further angle. The above process is repeated to obtain second moments $\sigma^2$ of scattering angle distribution at various angles and construct the second moments $\sigma^2$ of scattering angle distribution into a CT image of the examined object by using a CT reconstruction algorithm.

Figure 3:
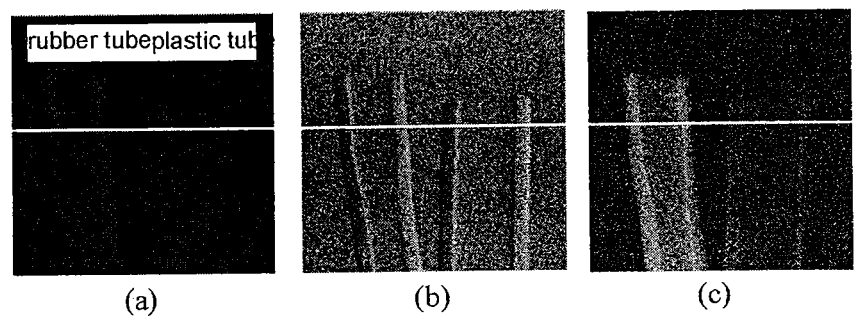
Figure 4:
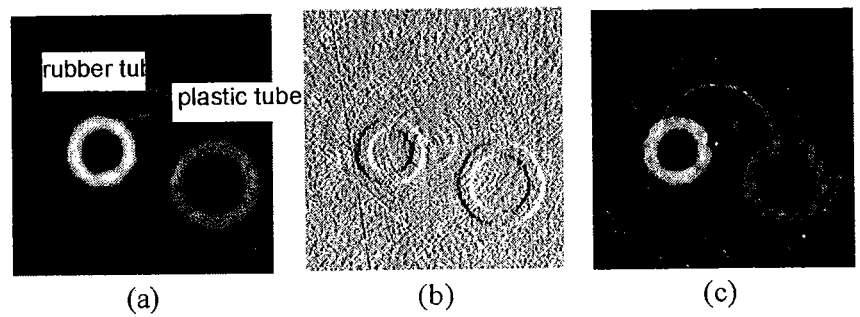

Described above is an image of the examined object established based on scattering simulation under x-ray irradiation (sp). As shown in FIG. 3, wherein FIG. 3a is an image of absorption, FIG. 3b is an image of differential phase information, and FIG. 3c is an image of dark-field information. As shown in FIG. 4, wherein FIG. 4a is an image of absorption, FIG. 4b is an image of differential phase information, and FIG. 4c is an image of dark-field information. Wherein the respective pictures shown in FIG. 4 are cross section figures of the examined object along the marked white lines as shown in FIG. 3.

Here, a generalized scattering parameter $f_s$ is used to describe the small-angle scattering property of a sample substance for x-rays, which resembles description of the attenuation (including absorbing and scattering functions) property of a substance for x-rays using a linear attenuation coefficient. Thus, by comparing decreases in the contrast ratio of the intensity curve at a certain pixel point on the detector, the scattering information for a certain corresponding point on the examined object can be indirectly obtained. Therein, a relationship between the second moment $\sigma^2$ of the scattering angle distribution and the generalized scattering parameter $f_s$ is known as:

$$\sigma^2 = \int_L f_s(l)\,dl = \int_L \frac{\rho_n(l)\sigma_s(l)}{2\alpha_p}\,dl \quad (5)$$

Therein, L is a distance from the radiation source to the first grating, l is an integration variable, $\rho_n$ is a substance density, $\sigma_s$ is a scattering cross section, and $\alpha_p$ is a broadening width of a single spherical scattering body for radiation. It can be seen that the generalized scattering parameter is associated with physical quantities such as substance density $\rho_n$, scattering cross section $\sigma_s$, broadening width $\alpha_p$ of a single spherical scattering body for radiation.

Hence, the image reconstructed based on the second moment $\sigma^2$ of the scattering angle distribution reflects a distribution status of the generalized scattering parameter $f_s$. This is highly effective for the object detection. As shown in FIGS. 3 and 4 for example, the differences between a rubber tube and a plastic tube images are presented in contrast more clearly.

Although the present invention is described based on an incoherent x-ray source, the concept and principle of the invention described above are in fact equally applicable to grating dark-field imaging using Talbot-Lau interferometry.

The x-ray dark-field imaging method set forth according to the present invention further improves the classic-optics-based grating imaging method such that it may execute the three of absorbing, phase contrast and dark-field imaging on the same system set. This immensely enriches the scope of selection for an imaging technology.

The grating dark-field imaging based on incoherent x-ray source may be applied to material science, medical imaging of tissues (e.g. breast) and other fields alike.

The invention claimed is:

1. An x-ray imaging system for performing an x-ray scattering imaging of an examined object, comprising:
   an x-ray source, a first and a second absorbing gratings, an x-ray detector, wherein the x-ray source, the first and second absorbing gratings are orderly located on a propagation direction of the x-rays;
   a data processor unit for processing data information;
   a reconstruction unit for reconstructing an image of the examined object; and
   a controller for controlling operations of the x-ray source, the first and second absorbing gratings, the x-ray detector and the data processor unit, so as to carry out the following processes:
   the x-ray source emits x-rays to an examined object;
   one of the two absorbing gratings performs phase stepping motions within at least one of its cycles;
   in each phase stepping motion, the detector receives the x-ray and converts it into an electric signal; wherein through the phase stepping motion of at least one cycle, the x-ray intensity at each pixel point on the detector is represented as an intensity curve;
   the intensity curve at each pixel point on the detector is compared to an intensity curve in the absence of the examined object, to acquire a variation in the contrast ratio of the intensity curves;
   a second moment of scattering angle distribution for each pixel on the detector is calculated from the intensity curve variation; and
   pixel values of the examined object are obtained from the second moment of scattering angle distribution, whereby an image of the examined object is reconstructed from the pixel values of the examined object obtained from the second moment of scattering angle distribution.

2. The system according to claim 1, wherein the x-ray source is a small focal spot source.

3. The system according to claim 1, wherein the x-ray source, the first and second absorbing gratings, and the x-ray detector are arranged according to the following relationship:

$$\frac{p_1}{p_2} = \frac{L}{L+D}$$

wherein $p_1$ and $p_2$ represent respectively the cycles of the first and second absorbing gratings, L is a distance between the x-ray source and the first grating, and D is a distance between the first and the second absorbing gratings.

4. The system according to claim 1, wherein the system further comprises a rotation device for enabling the examined object to rotate an angle under the control of the controller.

5. The system according to claim 4, wherein second moments of x-ray scattering distribution at various angles are obtained, and an image of the examined object is reconstructed in accordance with a CT image reconstruction algorithm, wherein the reconstruction algorithm makes use of the following formula:

$$\sigma^2 = \int_L f_s(l)\,dl$$

wherein $\sigma^2$ is the second moment of the scattering angle distribution, L is a distance from the radiation source to the first grating, l is an integration variable, and $f_s$ is a generalized scattering parameter.

6. The system according to claim 1, wherein the intensity curves for a certain pixel point on the detector with and without the presence of the examined object are represented respectively as follows:

$$I_s(k) \approx a_s + b_s \cos(k\Delta x + \phi_s) \text{ and}$$

$$I_b(k) \approx a_b + b_b \cos(k\Delta x + \phi_b)$$

wherein $\Delta x$ is a stepping length, a phase difference between the two intensity curves is $\Delta\phi = (\phi_s - \phi_b)$, $I_s$ is the intensity curve for a certain pixel point on the detector with the presence of the examined object, $I_b$ is the intensity curve for a certain pixel point on the detector without the presence of the examined object, $a_s$ is an average value of the intensity curve with the presence of the examined object, $b_s$ is the magnitude of the intensity curve with the presence of the examined object, $a_b$ is an average value of the intensity curve without the presence of the examined object, $b_b$ is the magnitude of the intensity curve without the presence of the examined object $\phi_s$ is the phase of the intensity curve with the presence of the examined object, $\phi_b$ is the phase of the intensity curve without the presence of the examined object, and k represents the $k^{th}$ step.

7. The system according to claim 6, wherein a contrast ratio of the intensity curve is represented as:

$$V = \frac{I_{max} - I_{min}}{I_{max} + I_{min}}$$

wherein $I_{max}$ and $I_{min}$ represent respectively the maximum and the minimum values of the intensity curve.

8. The system according to claim 7, wherein a quantitative relationship between the second moment of the scattering angle distribution and the contrast ratio of the intensity curves is represented as follows:

$$\sigma^2 = -\frac{1}{2\pi^2}\left(\frac{p_2}{D}\right)^2 \ln\left(\frac{V_s}{V_r}\right)$$

wherein $V_s$ and $V_r$ represent respectively contrast ratios of the intensity curves for a certain point on the detector, with and without the presence of the examined object, $p_2$ is a cycle of the second absorbing grating, D is a distance between the first and second absorbing gratings, and $\sigma^2$ is the second moment of the scattering angle distribution.

9. The system according to claim 1, wherein the system further comprises an imaging unit for displaying an image of the examined object.

10. The system according to claim 1, wherein the x-rays are incoherent x-rays.

11. The system according to claim 1, wherein the data processor unit and the controller are integrated together to be implemented by an all-purpose or dedicated processor.

12. The system according to claim 1, wherein the x-ray source is a large focal spot source.

13. The system according to claim 12, further comprising a source grating for dividing the x-rays emitted by the x-ray source into a plurality of small focal spot x-ray sources.

14. A method for imaging an examined object with an x-ray grating imaging system, wherein the x-ray grating imaging system comprises: an x-ray source, a first and a second absorbing gratings, an x-ray detector, a controller and a data processing unit;

wherein, the method comprises the steps of:
emitting x-rays to the examined object;
enabling one of the two absorbing gratings to perform phase stepping motions within at least one of its cycles; wherein each phase stepping step, the detector receives the x-ray and converts it into an electric signal; wherein through the phase stepping of at least one cycle, the x-ray intensity at each pixel point on the detector is represented as an intensity curve;
comparing the intensity curve at each pixel point on the detector to an intensity curve in the absence of the examined object to acquire a variation in the contrast ratio of the intensity curves;
calculating a second moment of scattering angle distribution for each pixel on the detector from the intensity curve variation;
obtaining pixel values of the examined object from the second moments of scattering angle distribution; and
reconstructing an image of the examined object from the pixel values of the examined object from the second moments of scattering angle distribution.

15. The method according to claim 14, comprising:
rotating the examined object;
repeating the steps of claim 12 at each rotation angle to thereby obtain second moments of x-ray scattering distribution at various angles; and reconstructing an image of the examined object in accordance with a CT image reconstruction algorithm, wherein the reconstruction algorithm makes use of the following formula:

$$\sigma^2 = \int_L f_s(l)\,dl$$

wherein $\sigma^2$ is the second moment of the scattering angle distribution, L is a distance from the radiation source to the first grating, l is an integration variable, and $f_s$ is a generalized scattering parameter.

16. The method according to claim 14, wherein the x-rays are incoherent x-rays.

* * * * *